United States Patent [19]

Funk, Sr.

[11] Patent Number: 5,199,973
[45] Date of Patent: Apr. 6, 1993

[54] METHOD OF DISPOSING OF MEDICAL SHARPS

[76] Inventor: Charles F. Funk, Sr., P.O. Box 6513, Gulfport, Miss. 39501

[21] Appl. No.: 891,933

[22] Filed: Jun. 1, 1992

Related U.S. Application Data

[63] Continuation-in-part of Ser. No. 562,886, Aug. 6, 1990, abandoned.

[51] Int. Cl.$^5$ .............................................. B65D 83/10
[52] U.S. Cl. ......................................... 75/392; 75/580; 75/959; 110/346
[58] Field of Search ........................ 75/959, 580, 392; 110/346

[56] References Cited

U.S. PATENT DOCUMENTS

| | | | |
|---|---|---|---|
| 2,369,112 | 2/1945 | Adeline | 75/27 |
| 2,370,610 | 2/1945 | Adeline | 75/27 |
| 4,842,138 | 6/1989 | Sandel et al. | 206/370 |
| 5,005,496 | 4/1991 | Nagata | 110/346 |

OTHER PUBLICATIONS

Kunes, Ellen–"The Trashing of America"–OMNI Feb. 1988–pp. 3–7.
"Final Infectious Waste Regulations"–BFI New Orleans–pp. 1–12.
BFI Waste Systems Browning-Ferris Industries–"EPC Guide for Infectious Waste Management"–U.S. Environmental Protection Agency Office May 1986.

*Primary Examiner*—Peter D. Rosenberg
*Attorney, Agent, or Firm*—Vaden, Eickenroht, Thompson, Boulware, & Feather

[57] ABSTRACT

A method of successfully disposing of, or recycling, waste metals comprising placing the waste metals in an aluminum container, placing the container in a crucible containing a mixture of powdered aluminum and iron oxide, initiating a self-sustaining reaction between the oxide and the metal that oxidizes the aluminum and reduces the iron and heats the contents of the crucible to 4,000° F. or higher to melt the waste metals and the iron and produce an ingot of the iron and the metal from the sharps and aluminum oxide slag, and trapping the heat and reaction products above the crucible with a hood of refractory material which covers the crucible and is sealed by partial immersion in loosely packed sand. The hood enables complete containment and incineration of the reaction products. The ingot and the slag can be recycled.

8 Claims, 2 Drawing Sheets

METHOD OF DISPOSING OF MEDICAL SHARPS

This application is a continuation-in-part of application Ser. No. 07/562,886, filed Aug. 6, 1990 entitled METHOD OF DISPOSING OF MEDICAL SHARPS, now abandoned.

This invention relates to a method of successfully disposing of or recycling metals and glass present in autoclave or incinerator and residue, treatment sludges, discarded batteries, medical "sharps", and other various products. The sharps in particular are rendered unrecognizable as potentially infectious biomedical waste and can be recycled.

In an article published in the February, 1988 issue of OMNI, Ellen Kunes in an article entitled "The Trashing of America" describes the problems being experienced at that time with what is now defined as "Potentially Infectious Biomedical Waste." In the article, she describes how children find boxes of used syringes in trash cans and play with them, thereby exposing themselves to infections and how hospital housekeeping staffs have the problem of being stuck by hypodermic needles that stick through plastic garbage bags. If any of these needles is contaminated, it could transmit to the person stuck an infectious disease, such as AIDS or the hepatitis B virus.

As a consequence, many states are passing laws that regulate the management of infectious waste, medical waste, and potentially infectious biomedical waste. The new regulations in Louisiana define potentially infectious biomedical waste, as including medical waste, infectious waste as defined herein and may be defined in other Louisiana law or code and waste considered likely to be infectious by virtue of what it is or how it may have been generated in the context of health care or health care-like activities. The regulation goes on to list what is included and one of the items is "sharps used or generated in health care or laboratory settings." Sharps are defined as needles, syringes, scalpels, scalpel blades, pipettes and other medical instruments capable of puncturing or lacerating skin. This definition also includes glass fragments and other health care and laboratory waste capable of puncturing or lacerating skin. The treatment for the various types of waste and specifically for sharps is that they be treated by incineration, encapsulation, or other means by which they are rendered unrecognizable as potentially infectious biomedical waste or otherwise unusable. The regulations require certain types of packaging. For sharps, it is required that they be placed in a break-resistant, rigid, puncture-resistant container, the openings of which must be tightly closed prior to storage or transport.

It is an object of this invention to provide a method of disposing of or recycling waste metals that is quick, effective, inexpensive, and non-polluting and that can be practiced by a hospital or any other producer of waste metal, in most cases, on its own grounds and that produces a valuable bi-product.

It is a further object of this invention to provide a method of disposing of or recycling waste material including potentially infectious riomedical waste such as sharps by exposing the waste metals to the heat produced by the exothermic reaction of aluminum and iron oxide in a reactor that will burn completely the non-metallic waste melt and sterilize the glass, and melt and sterilize the waste metals into a homogeneous body of low-grade steel that is covered by a slag layer of aluminum oxide. Both the steel and the slag can be into useful products.

These other objects, advantages, and features of this invention be apparent to those skilled in the art from a consider of this specification, including the attached drawings and appended claims.

IN THE DRAWINGS

Figure 1:
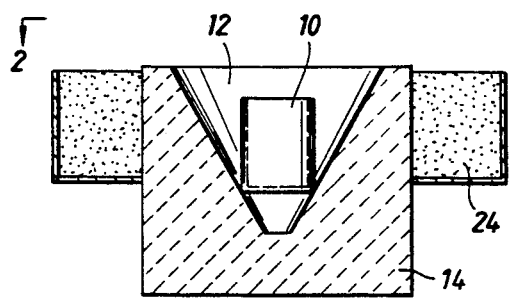
FIG. 1 is vertical, sectional view of the crucible, contained by a bed of sand, with a container of waste metals in its cavity.
Figure 3:
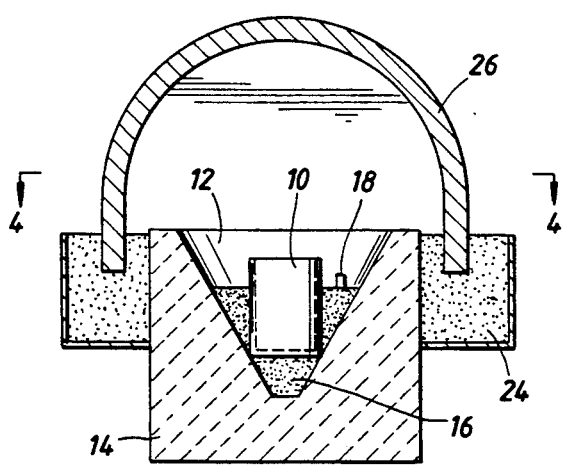

FIG. 3 a sectional view of the crucible of FIG. 1 after the mixture of aluminum and metal oxide has been placed in the crucible and the hood has been placed over the crucible and partially immersed in sand.

Figure 4:
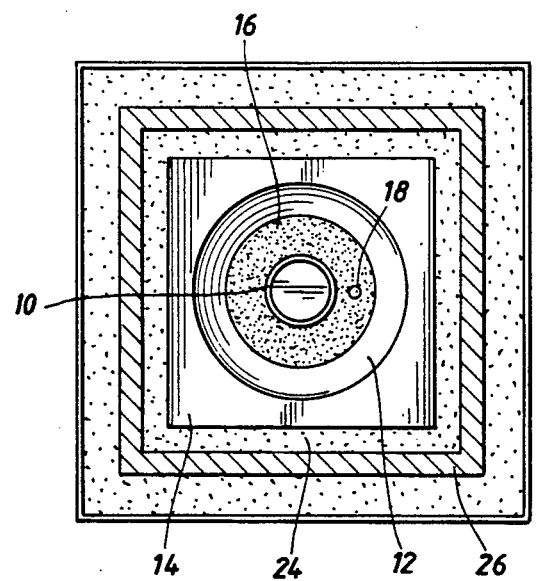

FIG. 4 is a view of FIG. 3 looking in the direction of arrows 4—4.

Figure 5:
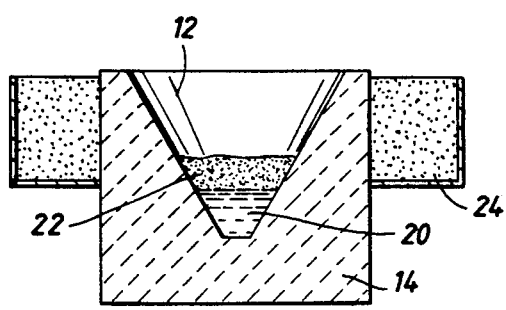
Figure 5:
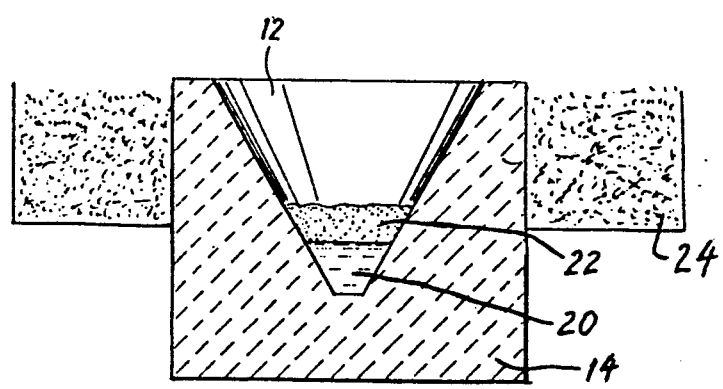

FIG. 5 shows the metal ingot and slag resulting from the reaction.

The method of this invention employs Thermit, which is a trademark for a mixture of aluminum powder and powdered iron oxide. When the mixture is caused to react, by strong heating, a great deal of heat evolves and aluminum oxide and a white hot molten mass of metallic iron are produced. The superheated liquid metal produced by the reaction is estimated to reach up to 5,000° F. (2,760° C.). The reaction is completed in 30 seconds to two minutes regardless of the size of the charge.

In accordance with this invention, container 10 is placed in cavity 12 of crucible 14, as shown in FIG. 1. Preferably the container is made out of aluminum and it is contemplated that such aluminum containers will be provided to the hospitals, laboratories and other producers of waste metals so that the once used needles, scalpels, or other waste metals can be immediately deposited in the aluminum container. Periodically these containers will be gathered up and taken to crucible 14 where, in the case of sharps, they will be rendered unrecognizable as potentially infectious biomedical waste or otherwise unusable. The aluminum containers would meet the requirement of the regulations that the containers for sharps be break-resistant and puncture resistant. Also, by using aluminum containers, the aluminum is oxidized by the reaction along with the powdered aluminum in the Thermit material and, therefore, does not introduce any foreign substance into the resulting ingot and slag.

Figure 2:
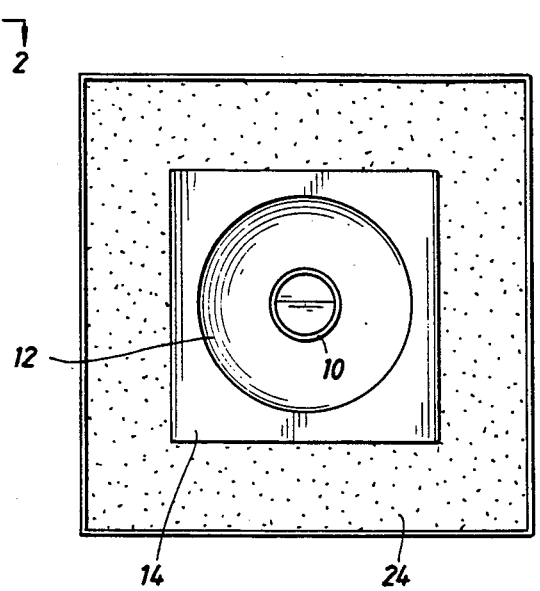
FIG. 2 is a view of FIG. 1 looking in the direction of arrows 2—2.

In FIG. 1, container 10 filled with waste metals is placed in cavity 12 of crucible 14. In the embodiment shown, cavity 12 is in the shape of an inverted cone, which is preferred because it will allow the resulting ingot and slag to be more readily removed from the cavity after the reaction is completed. Crucible 14 is contained in a bed of loose sand 24. In FIG. 2, the container is shown as being cylindrical. In FIG. 3, the Thermit mixture of powdered aluminum and iron oxide is placed in the crucible and is indicated by the number 16. Igniter 18, usually a thin ribbon of magnesium, extends into the Thermit mixture. The igniter produces sufficient heat to cause the aluminum in the mixture to begin to remove the oxygen from the iron oxide thereby initiating the exothermic reaction that produces aluminum oxide and iron and a lot of heat. The oxide/metal reaction provides its own oxygen supply and thus is virtually impossible to stop once the reaction has started. The temperature produced is 4,000°-5,000° F. which is sufficient to melt the stainless steel used in the sharps. The stainless steel joins the molten mass of iron produced to provide an ingot containing iron, chrome, and nickel from the iron oxide and the stainless steel Hood 26 is placed over crucible 14 and partially immersed in bed 24 of sand. The hood traps the heat and reaction products produced, thus eliminating air pollution. The metal settles to the bottom of the crucible and forms ingot 20. The aluminum oxide rises to the top of the molten metal and forms layer 22 of slag 22. Both of these products can be marketed. The iron, chrome, and nickel mixture can be recycled. The aluminum oxide or slag can be crushed and used in the manufacture of grinding wheels or any other application where an excellent abrasive is required. The intense heat produced by the reaction, of course, kills any viruses that may be associated with the sharps so the products produced can be reused safely.

Any organic material included with the medical waste will, of course, be burned in the process.

From the foregoing it will be seen that this invention is one well adapted to attain all of the ends and objects hereinabove set forth, together with other advantages which are obvious and which are inherent to the method.

What is claimed is:

1. A method of disposing of waste metals comprising placing the waste metals in a crucible of refractory material, placing a mixture of aluminum powder and iron oxide in the crucible, and igniting the mixture to produce an exothermic reaction that will raise the temperature of the waste metals above their melting point, reduce the iron oxide, and oxidize the aluminum.

2. The method of claim 1 in which the waste metals are collected in an aluminum container and the container containing the waste metals is placed in the reactor.

3. A method of disposing of waste metals comprising placing the waste metals in an aluminum container, placing the container in a crucible, placing a mixture of powdered aluminum and iron oxide in the crucible, and igniting the mixture to start an oxide/metal reaction that produces a temperature above 4,000° F. to melt the waste metals and the iron and produce an ingot of iron and aluminum-oxide slag.

4. A method of recycling waste metals comprising placing the waste metals in a crucible of refractory material, placing a mixture of aluminum powder and iron oxide in the crucible, igniting the mixture to produce an exothermic reaction that will raise the temperature of the waste metals above their melting point, reduce the iron oxide, and oxidize the aluminum, and trapping the heat and reaction products above the crucible enabling complete containment and incineration of the reaction products.

5. The method of claim 4 in which the waste metals are collected in an aluminum container and the container containing the waste metals is placed in the reactor.

6. The method of claim 4 in which the heat and reaction products are trapped by a hood of refractory material covering the crucible and sealed by partial immersion in an inert insulating material.

7. The method of claim 6 in which the inert insulating material is loosely packed sand.

8. A method of recycling waste metals comprising placing the waste metals in an aluminum container, placing the container in a crucible, placing a mixture of powdered aluminum and iron oxide in the crucible, igniting the mixture to start an oxide/metal reaction that produces a temperature above 4,000° F. to melt the waste metals and the iron and produce an ingot of iron and aluminum oxide slag, and trapping the heat and reaction products above the crucible enabling complete containment and incineration of the reaction products.

* * * * *